US00PP09887P

United States Patent [19]

Guillou

[11] Patent Number: Plant 9,887

[45] Date of Patent: May 6, 1997

[54] GERANIUM PLANT NAMED 'GUIRAC'

[75] Inventor: Bernard Guillou, Saint-Malo, France

[73] Assignee: ETS Guillou Freres, Saint-Malo, France

[21] Appl. No.: 592,238

[22] Filed: Jan. 26, 1996

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Foley & Lardner

[57] ABSTRACT

A new and distinct cultivar of geranium plant named 'Guirac,' characterized by its double-type red flowers, medium-green foliage, zonation around the base of the upper side of the leaf that is moderately conspicuous and moderately compact plant habit with excellent branching.

3 Drawing Sheets

The present invention comprises a new and distinct cultivar of geranium, botanically known as *Pelargonium peltatum*, and hereinafer referred to by the cultivar name 'Guirac'.

'Guirac' is a product of planned breeding program which had the objective of creating new geranium cultivars with double red flowers and leaves with a zonation.

'Guirac' was originated from a hybridization made in a controlled breeding program in Saint Malo, Bretagne, France in 1989. The female and male parents were unnamed hybrids from the proprietary Guillou collection, both parents being characterized by red, double-type flowers and leaves with zonation.

'Guirac' was discovered and selected as one flowering plant within the progeny of the stated cross by the inventor in 1989 in a controlled environment in Saint Malo, Bretagne, France.

The first act of asexual reproduction of 'Guirac' was accomplished when vegetative cuttings were taken from the initial selection in 1993 in a controlled environment in Saint Malo, Bretagne, France by a technician working under the supervision of the inventor. Horticultural examination of seleced units initiated in 1994 in Hannover, Germany has demonstrated that the combination of characteristics as herein disclosed for 'Guirac' are firmly fixed and are retained through successive generations of asexual reproduction. 'Guirac' has not been observed under all possible environmental conditions. The phenotype may vary with variations in environment such as temperature, light intensity, and day length without a change in genotype. The following observations, measurements, and comparisons describe plants grown in Hannover, Germany under greenhouse conditions which approximate those generally used in commercial practice.

The following traits have been repeatedly observed and are determined to be basic chaacteristics of 'Guirac' which in combination distinguish this geranium as a new distinct cultivar.

1. Double-type flowers.
2. Red flowers.
3. Medium-green foliage.
4. Zonation around the base on the upper side of the leaf is moderately conspicuous.
5. Moderately compact plant habit.
6. Well branched plant habit.

Of the many commercial cultivars known to the present inventor, the most similar in comparison to 'Guirac' is 'Tavira.' In comparison to 'Tavira,' 'Guirac' has more visible zonation near the base of the upper side of the leaf. 'Guirac' has narrow ellipitc flower buds while 'Tavira' has regular elliptic flower buds.

The accompanying drawing(s) show typical flower and foliage characteristics of 'Guirac'.

Figure 1:
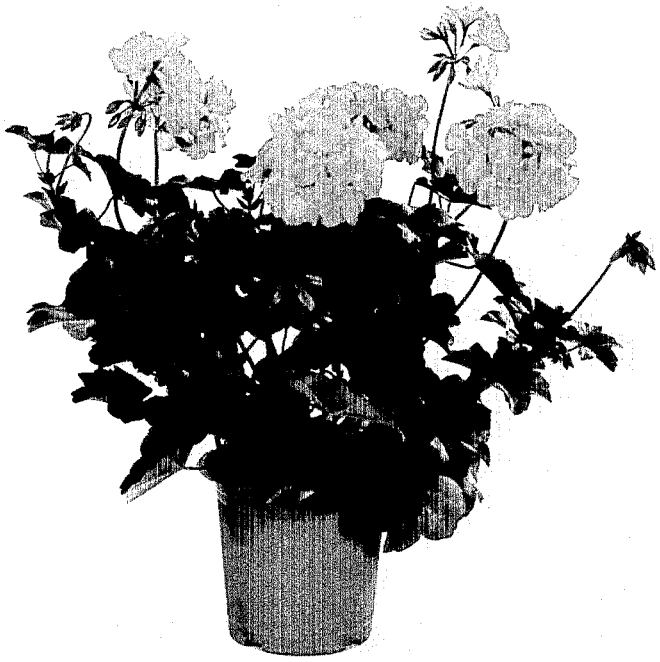
FIG. 1 is a side view of the cultivar.
Figure 2:
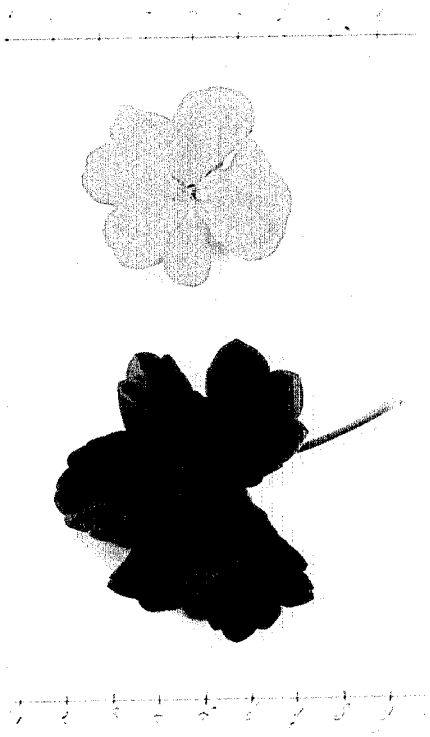
FIG. 2 is a view of the upper side of a typical leaf and flower of the cultivar.
Figure 3:
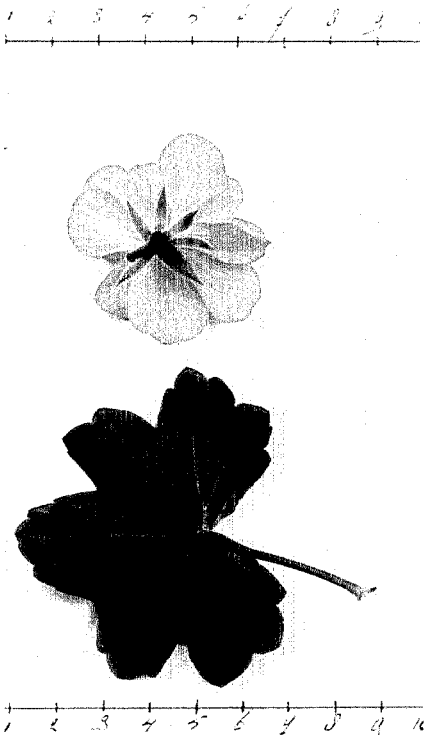
FIG. 3 is a view of the under side of a typical leaf and flower of 'Guirac'.

In the following description color references are made to The Royal Horticultural Society (R.H.S.) Colour Chart. The color values were determined between in 1994 under greenhouse conditions at in Hannover, Germany.

Classification:

*Botanical.*—*Pelargonium peltatum.*

*Commercial.*—Ivy geranium cultivar 'Guirac'.

INFLORESCENCE:

A. Umbel:
- *Average diameter.*—Approximately 92 mm.
- *Average depth.*—Approximately 40 mm.
- *Peduncle length.*—Approximately 148 mm.
- *Pedical length.*—Approximately 10 mm.

B. Corolla:
- *Average diameter.*—Approximately 50 mm.
- *Form.*—Double-type with medium petals.
- *Color (general tonality from a distance of three meters)* .—Red.
- *Color (tip and center).*—Red, approximately R.H.S. 46C.
- *Color (base).*—Pink-red, approximately R.H.S. 52B.

C. Bud:
- *Shape.*—Narrow elliptic.
- *Color (immature).*—Green, no anthocyanin.
- *Color (mature).*—Red.

D. Reproductive organs:
- *Androecium.*—3–7 fertile anthers with white filaments and orange pollen.
- *Gynoecium.*—5–6 lobed stigma with red style and stigma.

E. Spring flowering response period: 1–6 umbels open 15 weeks after planting unrooted cuttings (pinched plants.)

F. Outdoor flower production: 80–90 umbels per plant from April/May throughout September/October.

G. Durability: Shatter resistance is good.

PLANT

A. Foliage:
- *Form.*—Ivy-shaped.
- *Margin.*—Open to closed base.

*Color (margin).*—Medium-green, approximately R.H.S. 138A.
*Color (center).*—Medium-green.
*Color (zonation).*—Reddish-brown, moderately conspicuousness.
*Tolerance of Botrytis.*—Good.

B. General appearance and form:
*Internode length.*—30–40 mm.
*Branching pattern.*—5–6 branches per plant.
*Height.*—50–60 cm. in August.

Information about the plant:
*Length of stem.*—Long.
*Color of stem.*—Green.

Information about the leaf blade:
*Length.*—Medium to long.
*Width.*—Medium.
*Base.*—Open to closed.
*Main color of upper side.*—Medium green.
*Variegation.*—Absent.
*Zone on upper side.*—Present.
*Conspicuousness of zone on upper side.*—Medium.
*Color of zone on upper side.*—Reddish-brown.
*Undulation of margin.*—Medium.

Information about the inflorescence:
*Number of open flowers.*—Small.
*Diameter of largest flower.*—Medium to large.
*Pedicel: color in middle third.*—Light red.
*Pedicel swelling.*—Present.
*Time of beginning of flowering.*—Early to medium.

Information about bud and flower:
*Shape of flower bud.*—Narrow and elliptic.
*Type of flower.*—Double.
*Number of petals of flower.*—Medium.
*Margin of petal.*—Entire.
*Width of upper petal.*—Medium.
*Upper petal.*—Color of margin of upper side: Red, R.H.S. 46C. Color of middle of upper side: Red, R.H.S. 46C. Color of lower side: pink-red, R.H.S. 52B. Markings: present. Type of marking: stripes. Conspicuousness of markings: weak. White zone at the base: absent.
*Lower petal.*—Color of margin of upper side: Red, R.H.S. 50A. Color of middle of upper side: Red, R.H.S. 50A. Color of lower side: dark pink-red, R.H.S. 46D. Markings: absent.
*Inner petal.*—Color of middle of upper side: Red, R.H.S. 50A. Markings: absent.

What is claimed is:

1. A new and distinct cultivar of geranium plant named 'Guirac,' as illustrated and described.

* * * * *